(12) United States Patent
Todd et al.

(10) Patent No.: US 11,527,331 B2
(45) Date of Patent: Dec. 13, 2022

(54) SYSTEM AND METHOD FOR DETERMINING THE EFFECTIVENESS OF MEDICATIONS USING GENETICS

(71) Applicant: Xact Laboratories, LLC, Twinsburg, OH (US)

(72) Inventors: Rob Todd, Doylestown, PA (US); Jerry Wrobel, Aurora, OH (US); John Pigott, Slyvania, OH (US)

(73) Assignee: Xact Laboratories, LLC, Twinsburg, OH (US)

( * ) Notice: Subject to any disclaimer, the term of this patent is extended or adjusted under 35 U.S.C. 154(b) by 674 days.

(21) Appl. No.: 16/441,597

(22) Filed: Jun. 14, 2019

(65) Prior Publication Data

US 2019/0385747 A1 Dec. 19, 2019

Related U.S. Application Data

(60) Provisional application No. 62/773,424, filed on Nov. 30, 2018, provisional application No. 62/685,479, filed on Jun. 15, 2018.

(51) Int. Cl.
*G16H 50/70* (2018.01)
*G16H 20/10* (2018.01)
(Continued)

(52) U.S. Cl.
CPC ............ *G16H 50/70* (2018.01); *G16B 20/00* (2019.02); *G16H 20/10* (2018.01); *G16H 50/20* (2018.01); *C12Q 2600/106* (2013.01); *C12Q 2600/118* (2013.01); *C12Q 2600/136* (2013.01); *C12Q 2600/156* (2013.01); *C12Q 2600/158* (2013.01); *G01N 33/68* (2013.01);
(Continued)

(58) Field of Classification Search
None
See application file for complete search history.

(56) References Cited

U.S. PATENT DOCUMENTS 6,315,720 B1 11/2001 Williams et al.
8,386,274 B1 2/2013 Pinsonneault
(Continued)

OTHER PUBLICATIONS

PJ Caraballo et al., Electronic Medical Record-Integrated Pharmacogenomics and Related Clinical Decision Support Concepts, Aug. 2017, Clinical Pharmacology & Therapeutics, vol. 102 No. 2, pp. 254-264 (Year: 2017).*
(Continued)

*Primary Examiner* — Evangeline Barr
*Assistant Examiner* — Karen A Hranek
(74) *Attorney, Agent, or Firm* — Standley Law Group LLP; Adam J. Smith; Jeffrey S. Standley (57) ABSTRACT

A system and method for alerting a healthcare provider to ineffective prescribed medications is provided. A laboratory system receives test results with genetic markers for a patient, queries a database containing medications known to be ineffective in persons having particular genetic markers to determine whether any medications prescribed by, or likely to be prescribed by, a healthcare provider to the patient are known to be ineffective in persons having the same genetic markers as the patient, and transmits an alert containing such information to a healthcare provider system for the healthcare provider.

12 Claims, 8 Drawing Sheets

(51) Int. Cl.
*G16H 15/00* (2018.01)
*G01N 33/68* (2006.01)
*G16H 10/60* (2018.01)
*G16H 80/00* (2018.01)
*G16H 70/40* (2018.01)
*G16B 20/00* (2019.01)
*G16H 50/20* (2018.01)

(52) U.S. Cl.
CPC ......... *G01N 2800/52* (2013.01); *G16H 10/60* (2018.01); *G16H 15/00* (2018.01); *G16H 70/40* (2018.01); *G16H 80/00* (2018.01)

(56) References Cited

U.S. PATENT DOCUMENTS

| | | | |
|---|---|---|---|
| 10,950,354 B1* | 3/2021 | Belgoroski | G16H 40/20 |
| 2002/0012921 A1 | 1/2002 | Stanton, Jr. | |
| 2002/0115073 A1 | 8/2002 | Papadopoulos et al. | |
| 2002/0147616 A1 | 10/2002 | Pollard et al. | |
| 2002/0187483 A1* | 12/2002 | Hoffman | G16B 20/00 435/6.16 |
| 2003/0040002 A1 | 2/2003 | Ledley | |
| 2005/0107672 A1 | 5/2005 | Lipscher et al. | |
| 2005/0149361 A1* | 7/2005 | Saus | G16H 70/40 705/3 |
| 2006/0259325 A1 | 11/2006 | Patterson | |
| 2007/0178501 A1 | 8/2007 | Rabinowitz et al. | |
| 2008/0091464 A1 | 4/2008 | Lipscher et al. | |
| 2008/0131887 A1 | 6/2008 | Stephan et al. | |
| 2008/0162352 A1 | 7/2008 | Gizewski | |
| 2008/0228824 A1 | 9/2008 | Kenedy et al. | |
| 2009/0094059 A1* | 4/2009 | Coleman | G16H 20/10 705/3 |
| 2009/0198519 A1 | 8/2009 | McNamar | |
| 2010/0070455 A1 | 3/2010 | Halperin et al. | |
| 2010/0317006 A1 | 12/2010 | Soykan et al. | |
| 2012/0065999 A1 | 3/2012 | Takatoku et al. | |
| 2012/0185270 A1 | 7/2012 | Scantland et al. | |
| 2013/0096943 A1 | 4/2013 | Carey et al. | |
| 2013/0246079 A1 | 9/2013 | Hoffman et al. | |
| 2014/0303992 A1 | 10/2014 | Scantland et al. | |
| 2014/0316821 A1* | 10/2014 | Sheffield | G16B 50/00 705/3 |
| 2014/0350954 A1* | 11/2014 | Ellis | G16H 10/60 705/2 |
| 2014/0372141 A1 | 12/2014 | Renner et al. | |
| 2015/0058030 A1 | 2/2015 | Scantland et al. | |
| 2015/0058039 A1* | 2/2015 | Shiloh | G16H 70/40 705/3 |
| 2015/0170291 A1 | 6/2015 | Renner et al. | |
| 2015/0228030 A1 | 8/2015 | Scantland et al. | |
| 2016/0048652 A1* | 2/2016 | Spivey | G16H 70/40 705/2 |
| 2016/0092652 A1 | 3/2016 | Stewart et al. | |
| 2016/0180063 A1 | 6/2016 | Scantland et al. | |
| 2016/0239636 A1* | 8/2016 | O'Donnell | G16B 20/20 |
| 2017/0004282 A1 | 1/2017 | Scantland et al. | |
| 2017/0046491 A1 | 2/2017 | Scantland et al. | |
| 2017/0046492 A1 | 2/2017 | Renner et al. | |
| 2017/0213011 A1 | 7/2017 | Hoffman et al. | |
| 2017/0270246 A1* | 9/2017 | Baskys | G16B 20/00 |
| 2017/0308669 A1* | 10/2017 | Apte | G16H 70/40 |
| 2018/0075220 A1 | 3/2018 | Hill, Sr. et al. | |
| 2018/0308569 A1* | 10/2018 | Luellen | G16H 40/20 |
| 2018/0330060 A1* | 11/2018 | Biles | G16H 50/30 |
| 2019/0244688 A1* | 8/2019 | Wilson | G16H 10/40 |

OTHER PUBLICATIONS

Hicks et al., Integrating pharmacogenomics into electronic health records with clinical decision support, Dec. 1, 2016, Am J Health Syst Pharm 73(23) (Year: 2016).*

Hinderer et al., Integrating clinical decision support systems for pharmacogenomic testing into clinical routine—a scoping review of designs of user-system interactions in recent system development, 2017, BMC Medical Informatics and Decision Making (Year: 2017).*

Clinisync, Clinisync Products and Services webpage, http://www.clinisync.org/, Jul. 18, 2018, 5 pages.

Althoff, Lisa, DNA Chip—Genetic Testing of the Future webpage, https://www.ndsu.edu/pubweb/~mcclean/plsc431/students99/althoff.html, Copyright 1999, Aug. 2, 2019, 5 pages.

Labx, DNA Sequencers Listings webpage, https://www.labx.com/dna-sequencers, Aug. 2, 2019, 3 pages.

VECNA, Vecna Patient Solutions webpage, https://healthcare.vecna.com/, Jul. 18, 2019, 11 pages.

Translational Software, Making Sense of Pharmacogenomics Testing webpage, https://translationalsoftware.com/, Sep. 11, 2019, 14 pages.

Translational Software, Integrated Into Clinical Systems archived webpage, https://web.archive.org/web/20171217010330/https://translationalsoftware.com/, Oct. 17, 2017, 7 pages.

Translational Software, Insights Ready for Action archived webpage, https://web.archive org/web/20180829020620/https://translationalsoftwarre.com/, Aug. 29, 2018, 9 pages.

Coriell Life Sciences, GeneDose—Medication Risk Management Tool archived webpage, https://web.archive.org/web/20170611205541/http://genedose.com/, Jun. 11, 2017, 8 pages.

Coriell Life Sciences, DNA-Driven Diagnostics To Guide Clinical Decision-Making webpage, https://www.coriell.com/genetic-interpretation-reporting/, Sep. 11, 2019, 9 pages.

Coriell Life Services, GeneDose Youtube Video, https://youtube.com/watch?v=tku6_9tADuw, Sep. 11, 2019.

* cited by examiner

SYSTEM AND METHOD FOR DETERMINING THE EFFECTIVENESS OF MEDICATIONS USING GENETICS

CROSS-REFERENCE TO RELATED APPLICATION

This application claims the benefit of U.S. Provisional Application Ser. No. 62/685,479 filed Jun. 15, 2018 and U.S. Provisional Application Ser. No. 62/773,424 filed Nov. 30, 2018, the disclosures of each of which are hereby incorporated by reference as if fully restated herein.

TECHNICAL FIELD

Exemplary embodiments relate generally to a system and method for determining the effectiveness of medications using genetics.

BACKGROUND AND SUMMARY OF THE INVENTION

A person visiting a doctor may present with one or more symptoms. Based on the symptoms presented, test results, or underlying conditions or diseases diagnosed, the person may be prescribed one or more medications by the healthcare provider as part of a treatment program. The medications prescribed may be selected based on the historical effectiveness of such medications for treating the symptoms presented by the person and/or the underlying disease or condition diagnosed by the healthcare provider. Traditionally, the prescription of medications is, at least initially, based on historical effectiveness. Individual prescriptions may be altered through a trial and error process following the initial prescription. For example, alternative medications or dosages may be prescribed where the prescription of a medication causes a side effect or allergic reaction in a patient. Over prescription or dosing of medications may cause side effects. Under prescription or dosing of medications may bring ineffective results or side effects.

A person's genetic makeup affects how the person responds to certain medications. For example, a person's genetic makeup may cause some medications or dosages to be wholly or partially ineffective. Prescription of medications to a person who has a genetic makeup that makes the medication wholly ineffective may waste resources and unnecessarily expose the person to the risk of side effects. Similarly, prescription of medications to a person who has a genetic makeup that makes the medication partially ineffective may result in less that desirable therapeutic effects or require a larger dosage to be effective. In some cases, alternative medications or dosages are available for use with the same, or similar, therapeutic effects.

For example, without limitation, a blood thinner may be known to reduce the risk of embolisms and may be prescribed to a person following stent placement. However, individual genetic makeup or physiology may alter the effectiveness of the prescribed blood thinner. For example, without limitation, the blood thinner may have a reduced effectiveness in persons carrying specific genetic markers. It would be desirable to substitute alternative medications or adjust the dosage of prescribed medications for persons having a genetic makeup which reduces the effectiveness of the prescribed medication. As a further example, again without limitation, the prescribed blood thinner may be wholly ineffective in persons carrying specific genetic markers. It would be desirable to substitute alternative medications, or find alternative treatment options, for persons having a genetic makeup which renders the prescribed medication ineffective. Therefore, what is needed is a system and method for determining the effectiveness of medications using genetics.

These disclosures provide a system and method for determining the effectiveness of medications using genetic data. A user's visit information may be reviewed to identify applicable tests. For example, such tests may indicate the presence or non-presence of genetic markers which may indicate a genetic makeup for a patient that may have a bearing on the effectiveness of one or more medications prescribed, or likely to be prescribed, to the user. The system may determine whether identified tests fits certain billing parameters. For example, the system may be configured to determine whether the identified tests are covered by the user's insurance. If the test for one or more markers does not fit the billing parameters, then the next genetic marker(s) may be considered. If the test does fit the billing parameters then the option to order testing may be presented to the healthcare provider. If selected, the appropriate marker(s) may be added to a testing device and the genetic testing may be performed.

To perform the testing, genetic material may be removed from the user. A testing device may be created to test for the specific genetic marker(s) ordered by the healthcare provider. The genetic material may be sequenced using the testing device and the presence or non-presence of the tested genetic markers may be determined. The results may be analyzed and ineffective medications may be identified. In exemplary embodiments, for each medication prescribed or likely to be prescribed, the presence or non-presence of a genetic marker may be compared against the medications known to be effective or ineffective in the presence of the given marker. Effective medications and/or dosages may be flagged. Alternatively, or additionally, ineffective medications and/or dosages may be flagged. For those medications and/or dosages determined to be ineffective, alternative medications, dosages, and/or treatment options may be suggested. Regardless, the testing results may be returned to the healthcare provider's system. For example, treatment of a particular disease may normally first begin with medication. However, if the person has a genetic makeup which would make such medication ineffective, a surgical option may instead be suggested.

The results may be returned to the healthcare provider in the form of an interface for display on an electronic display. The results may be displayed in a fashion which provides the clinical consequences of prescribing the medication. The interface may further provide indications of particular conditions and generate alerts when particular conditions are met. For example, without limitation, executable software instructions may be provided which configure the electronic display to display an interface comprising an explanation of the results, alerts, abnormal ranges, ineffective medications, potential interactions as understood in view of the analyzed genetic information, and other clinical information. This information may be transmitted with the results in a single file. In exemplary embodiments, these results and alerts may be integrated into the healthcare providers' electronic medical record system (EMR) by way of a single file. This information may be further transmitted to any number of healthcare provider facilities, such as but not limited to hospitals, by way of one or more healthcare information exchanges. For example, information may be transmitted to all healthcare providers treating the user. The results may also be stored for use by, and selective transmitted to, future healthcare providers.

Further features and advantages of the devices and systems disclosed herein, as well as the structure and operation of various aspects of the present disclosure, are described in detail below with reference to the accompanying figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Figure 1A:
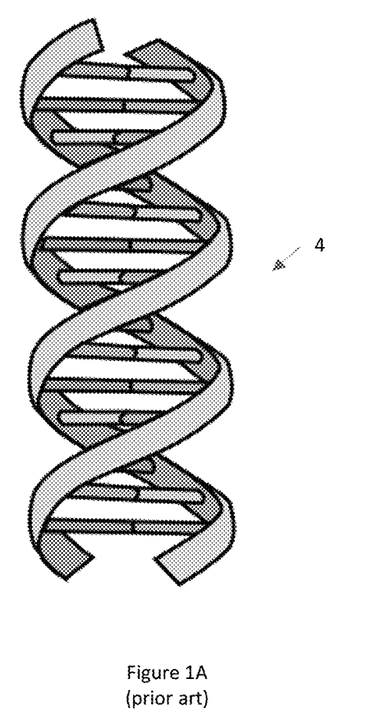
FIG. 1A is a simplified illustration of a DNA helix.

FIG. 1A is a simplified illustration of a DNA helix 4. DNA, or deoxyribonucleic acid, is a double-helix shaped chain of nucleotides that carry the genetic instructions used in the growth, development, functioning, and reproduction of all known living organisms. There are four major types of nucleobases in any nucleotide of a DNA sequence, which are generally coded as A, T, C, and G for adenine, thymine, cytosine, and guanine, respectively. Each individual human is believed to have a unique DNA structure that defines the persons' genetic makeup.

Figure 1B:
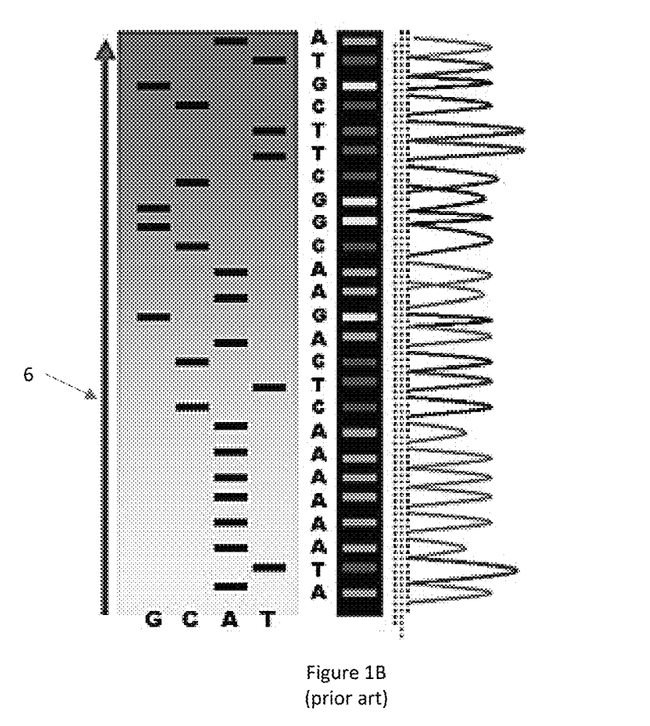
FIG. 1B is a simplified illustration of a DNA sequencing test result.

FIG. 1B is a simplified illustration of a DNA sequencing test result 6. Upon sequencing of the DNA, the presence or non-presence of particular nucleobases (A, T, C, or G) may be detected. The presence and non-presence or order of such nucleobases can be used to determine the presence or non-presence of certain genetic markers. The genetic markers may indicate the existence or non-existence of certain genetic traits for the person.

Figure 2:
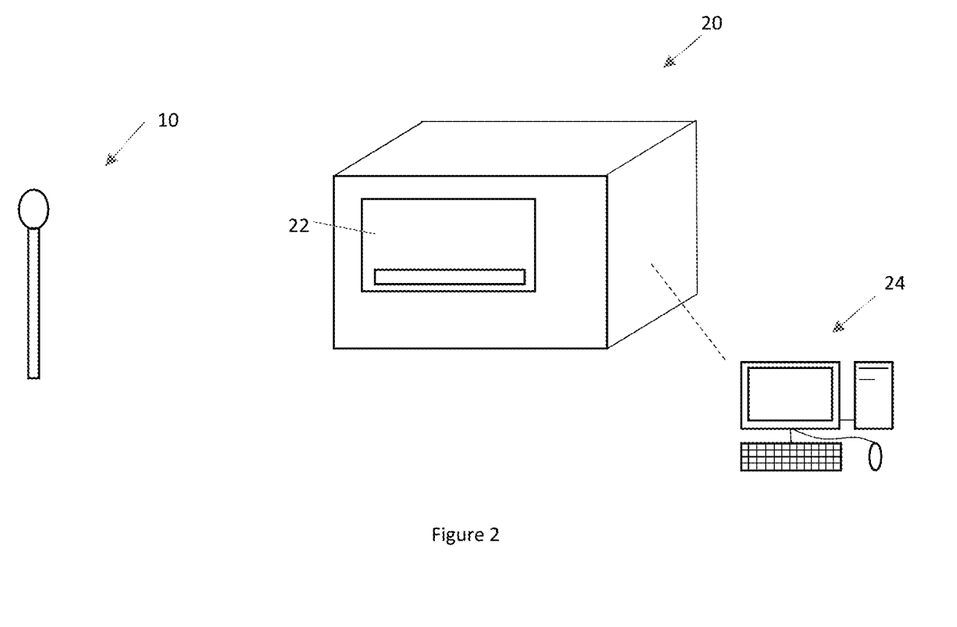
FIG. 2 is a simplified perspective view of an exemplary genetic material gathering device and an exemplary sequencing device.

FIG. 2 is a simplified perspective view of an exemplary genetic material gathering device 10 and an exemplary genetic sequencing device 20. The genetic material gathering device 10 may be a swab, syringe, vial, strip, or the like. For example, without limitation, the genetic material gathering device 10 may be a swab configured to be used on the inside of the user's cheek to gather saliva or skin cells. In other examples, without limitation, the genetic material gathering device 10 may be a syringe configured to gather blood, a vial configured to store blood, hair, skin samples, or the like. Any type of genetic material gathering device 10 for gathering any type of genetic material is contemplated.

The genetic sequencing device 20 may be any kind of device configured to sequence genetic material. In exemplary embodiments, the genetic sequencing device 20 may comprise a loading area 22 and a control panel 24. The loading area 22 may be configured to accept one or more testing devices 30. The control panel 24 may be integrally formed with the genetic sequencing device 20 or may be a separate electronic device in communication with the genetic sequencing device 20. The control panel 24 may be configured to accept user input comprising instructions for carrying out various genetic tests on the testing device 30. The control panel 24 may be figure configured to display the results of such testing. Such instructions may, alternatively or additionally, be accepted from a remote device. Testing results may be transmitted to a remote device.

Figure 3:
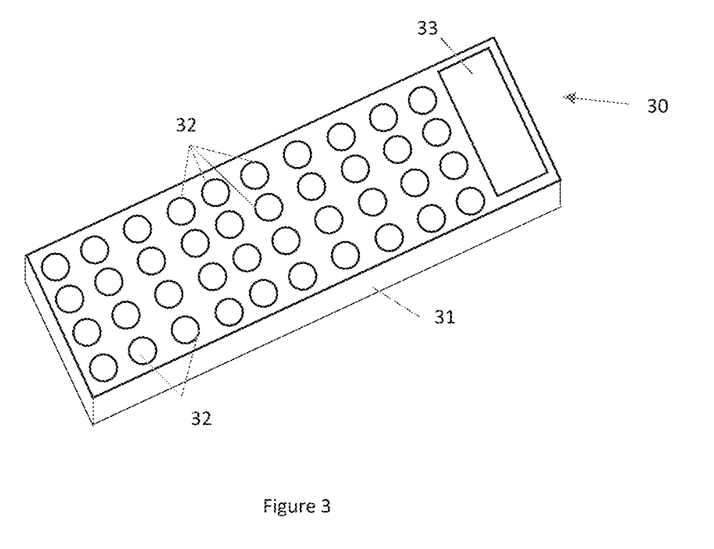
FIG. 3 is a simplified perspective view of an exemplary genetic testing device for use with the sequencing device of FIG. 2.

FIG. 3 is a simplified perspective view of an exemplary genetic testing device 30 for use with the sequencing device 20. In exemplary embodiments, the testing device 30 may be a chip 31 comprised of a number of wells 32, though any type of testing device 30 is contemplated. Each of said wells 32 may be configured to test for a particular genetic marker. The testing device 30 may be configured to accommodate any number of wells 32. In exemplary embodiments, certain wells 32 may be added or removed from the testing device 30 in order to test for the presence or non-presence of various genetic markers. For example, without limitation, wells 32 may be added to the chip 31 to test for particular genetic traits and wells 32 may be removed from the chip 31 if a particular genetic trait is not being tested for. In still other exemplary embodiments, the wells 32 being used may be placed in an unblocked position such that genetic material may enter the well 32. Similarly, the wells 32 not being used may be placed in a blocked position such that genetic material may not enter the wells 32. Modifications to the testing device 30 may be performed manually or automatically based on the instructions for testing received. For example, without limitation, the testing device 30 may be constructed or modified by one or more robots. The testing device 30 may further comprise one or more areas 33 to affix labels, markers, or the like.

Figure 4:
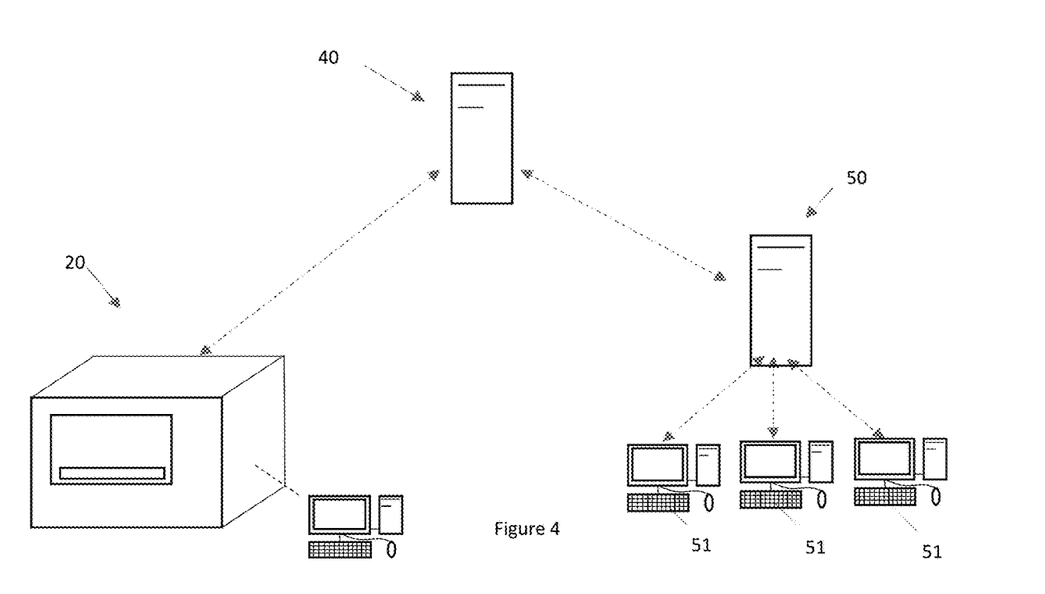
FIG. 4 is a simplified plan view of an exemplary system, including the sequencing device of FIG. 2.

FIG. 4 is a simplified plan view of an exemplary system. The genetic sequencing device 20 may be in electronic communication with a laboratory system 40. The laboratory system 40 may receive testing instructions which are communicated to the genetic sequencing device 20. The laboratory system 40 may also be configured to receive the results of any performed tests from the genetic sequencing device 20. In exemplary embodiments, the laboratory system 40 may be a laboratory facing system. The laboratory system 40 may be in electronic communication with a healthcare provider system 50. The healthcare provider system 50 may comprise patient information, test orders, and test results. The healthcare provider system 50 may communicate the instructions for testing to the laboratory system 40. The test results may be transmitted from the laboratory system 40 to the healthcare provider system 50. In exemplary embodiments, the healthcare provider system 50 may be a healthcare provider facing system such as, but not limited to, an electronic medical record ("EMR") system or the like. Although a single genetic sequencing device 20, laboratory system 40, and healthcare provider system 50 are shown, any number of such components is contemplated.

The sequencing device 20, the laboratory device 40, and the healthcare provider system 50 may be located in the same facility, or may be remote from one another. The electronic communication may be by way of a wired or a wireless connection. The electronic communication may further be made by way of one or more network interface devices and one or more communication networks located at each of the sequencing device 20, the laboratory device 40, and the healthcare provider system 50. The communications networks utilized may include, but are not limited to, the internet, intranet, cellular network, or the like. In exemplary embodiments, communications between the genetic sequencing device 20, the laboratory system 40, and/or the healthcare provider system 50 may be made secured and encrypted. Alternatively, or in addition, such communications may be made in a standardized format such as, but not limited to, a HL7 format. In exemplary embodiments, the test results may be pulled from the laboratory system 40 such as, but not limited, to by the use of scanning and archiving software. The testing results may be automatically integrated into the healthcare provider's system 50. Such integration may be performed by way of a flat file, though any method of integration is contemplated. For example, without limitation, the testing results may be automatically integrated into the EMR utilized by the healthcare provider's system 50.

Alternatively, or in addition, the testing results may be made available to the healthcare provider by way of an internet-based portal accessed through the healthcare provider's system 50 or any number of personal electronic devices 51. In particular, a hyperlink to the portal may be provided to the healthcare provider's system 50 such that it is stored as a quick link access, though such is not required. As yet another example, without limitation, the testing results may be provided to the healthcare provider by way of email to the healthcare provider system 50. In other embodiments, the testing results may be made available to the healthcare provider by way of an application installed on the various personal electronic devices 51.

The testing results stored on the laboratory system 40 may be secured such that a particular healthcare provider can only access the results for users associated with the particular healthcare provider. For example, without limitation, permission may be set such that login credentials associated with a given healthcare provider may be permit access to test results for particular users associated with that healthcare provider. The laboratory system 40 may be configured to periodically download testing results from the genetic sequencing device 20. Similarly, the laboratory system 40 may be configured to periodically download testing results to the healthcare providers system 50. Alternatively, or in addition, certain results may be downloaded on demand.

Each of the sequencing device 20, the laboratory device 40, and the healthcare provider system 50 may comprise one or more electronic components. Such electronic components may include, but are not limited to, processors, electronic storage devices, user input devices, displays, and the like. Each of the sequencing device 20, the laboratory device 40, and the healthcare provider system 50 may comprise software instructions configured to perform the steps and functions described herein.

Figure 5:
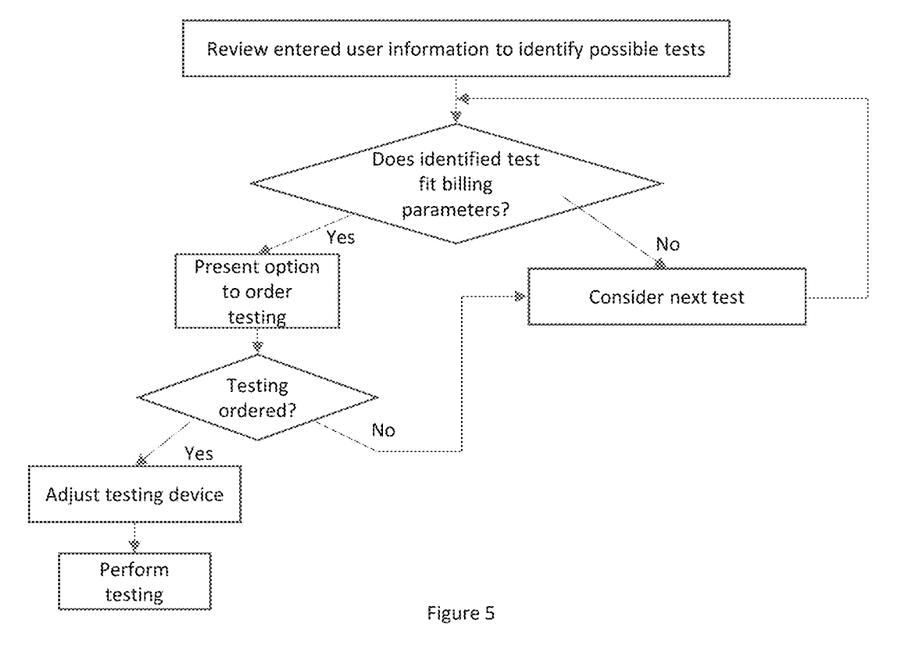
FIG. 5 is a simplified block diagram illustrating exemplary logic for identifying, ordering, and performing tests.

FIG. 5 is a simplified block diagram illustrating exemplary logic for identifying, ordering, and performing tests. A user may visit one or more healthcare providers and present with a variety of symptoms. As the healthcare provider evaluates the user, including by taking a medical history, evaluating symptoms, and performing tests, the healthcare provider may enter information about the user into the healthcare providers' system 50. Already existing information about the user may already be present on the healthcare providers' system 50, though such is not required. Such information already existing or entered by the healthcare provider might include, for example but without limitation, demographic information, insurance information, medical history, known allergies, family history, some combination thereof, and the like. In exemplary embodiments, the healthcare providers' system 50 is an EMR. The entered information by the healthcare provider at a given visit may include, for example but without limitation, treatment actions taken, symptoms presented, diagnosed diseases or conditions, tests ordered, testing results, some combination thereof, and the like.

In exemplary embodiments, certain information about the user may be pulled by the laboratory system 40 from the healthcare provider's system 50 such as, but not limited, to by the use of scanning and archiving software. The laboratory system 40 may review the entered information and identify conditions diagnosed, or likely to be diagnosed, medications prescribed, or likely to be prescribed, to the user. The medications likely to be prescribed may be determined by comparing the entered information with standard treatment procedures. Such standard treatment procedures may be stored on the laboratory system 40, or one or more separate databases, and may be sourced from public and private data sources. For example, without limitation, if a stent placement is ordered for the user, the laboratory system 40 may determine that post-operative blood thinners are likely to be prescribed to the user. The conditions likely to be diagnosed may be determined by comparing the entered information, such as symptoms and test results, with diseases associated with such information. Such disease information may be stored on the laboratory system 40, or one or more separate database, and may be sourced from public and private data sources. For example, without limitation, if chest pain is reported, a likely condition of heart disease may be determined.

The laboratory system 40 may identify one or more genetic markers for testing that may have a bearing on the effectiveness of prescribed, or likely to be prescribed, medications. The laboratory system 40 may determine whether testing for the identified genetic markers fits one or more billing parameters. For example, without limitation, the laboratory system 40 may determine whether such testing would be considered medically necessary under Medicare regulations and/or guidelines. An exemplary listing of medically necessary codes is provided in tables 1-2 below. The provided tables are merely exemplary and are not intended to be limiting.

TABLE 1

Cardiovascular Diagnostic Codes

| Code | Description |
|---|---|
| 120.0 | Unstable angina |
| 120.1 | Angina pectoris with documented spasm |
| 120.8 | Other forms of angina pectoris |
| 120.9 | Angina pectoris, unspecified |
| 121.09 | ST elevation (STEMI) myocardial infarction involving other coronary artery of anterior wall |
| 121.11 | ST elevation (STEMI) myocardial infarction involving right coronary artery |
| 121.19 | ST elevation (STEMI) myocardial infarction involving other coronary artery |
| 121.29 | ST elevation (STEMI) myocardial infarction involving other sites |
| 121.3 | ST elevation (STEMI) myocardial infarction of unspecified site |
| 121.4 | Non-ST elevation (NSTEMI) myocardial infarction |
| 124.0 | Acute coronary thrombosis not resulting in myocardial infarction |
| 124.1 | Dressler's syndrome |
| 124.8 | Other forms of acute ischemic heart disease |
| 124.9 | Acute ischemic heart disease, unspecified |
| 125.110 | Atherosclerotic heart disease of native coronary artery with unstable angina pectoris |
| 125.700 | Atherosclerosis of coronary artery bypass graft(s), unspecified, with unstable angina pectoris |
| 125.710 | Atherosclerosis of autologous vein coronary artery bypass graft(s) with unstable angina |
| 125.720 | Atherosclerosis of autologous artery coronary artery bypass graft(s) with unstable angina pectoris |
| 125.730 | Atherosclerosis of nonautologous biological coronary artery bypass graft(s) with unstable angina pectoris |
| 125.750 | Atherosclerosis of native coronary artery of transplanted heart with unstable angina |
| 125.760 | Atherosclerosis of bypass graft of coronary artery of transplanted heart with unstable angina |
| 125.790 | Atherosclerosis of other coronary artery bypass graft(s) with unstable angina pectoris |

TABLE 2

Psychiatric and Pain Management Diagnostic Codes

| Code | Description |
|---|---|
| F31.30 | Bipolar disorder, current episode depressed, mild or moderate severity, unspecified |
| F31.31 | Bipolar disorder, current episode depressed, mild |
| F31.32 | Bipolar disorder, current episode depressed, moderate |
| F31.4 | Bipolar disorder, current episode depressed, severe, without psychotic features |
| F31.5 | Bipolar disorder, current episode depressed, severe, with psychotic features |
| F31.60 | Bipolar disorder, current episode mixed, unspecified |
| F31.61 | Bipolar disorder, current episode mixed, mild |
| F31.62 | Bipolar disorder, current episode mixed, moderate |
| F31.63 | Bipolar disorder, current episode mixed, severe, without psychotic features |
| F31.64 | Bipolar disorder, current episode mixed, severe, with psychotic features |
| F31.75 | Bipolar disorder, in partial remission, most recent episode depressed |
| F31.76 | Bipolar disorder, in full remission, most recent episode depressed |
| F31.77 | Bipolar disorder, in partial remission, most recent episode mixed |
| F31.78 | Bipolar disorder, in full remission, most recent episode mixed |
| F31.9 | Bipolar disorder, unspecified |
| F32.9 | Major depressive disorder, single episode, unspecified |
| F33.0 | Major depressive disorder, recurrent, mild |
| F33.1 | Major depressive disorder, recurrent, moderate |
| F33.2 | Major depressive disorder, recurrent severe without psychotic features |
| F33.3 | Major depressive disorder, recurrent, severe with psychotic symptoms |
| F33.40 | Major depressive disorder, recurrent, in remission, unspecified |
| F33.41 | Major depressive disorder, recurrent, in partial remission |
| F33.42 | Major depressive disorder, recurrent, in full remission |
| F33.9 | Major depressive disorder, recurrent, unspecified |
| G10 | Huntington's disease |

In exemplary embodiments, if any of the diagnostic codes are provided by the healthcare provider system 50 fit the provided billing parameters, then the genetic testing may automatically be included in the plan of treatment for that patient.

Alternatively, or in addition, the laboratory system 40 may be configured to gather and review insurance information for coverage eligibility for particular types of testing. The laboratory system 40 may be configured to determine whether such testing would be wholly or partially covered by the user's insurance. This may be performed by reviewing the billing codes against those codes covered by the user's insurance. This may alternatively or additionally be performed by interfacing with the user's insurance provider. Regardless, in such embodiments, the billing parameters may comprise the testing known or likely to be approved. These billing parameters may be predetermined and preprogramed and may be selected based on the user's insurance coverage.

Alternatively, or in addition, the laboratory system 40 may be configured to generate one or more forms for gathering and authorizing payment information for desired testing. For example, without limitation, the laboratory system 40, or a separate payment system, may be configured to store and authorize credit card transactions to pay for the ordered testing. This option may be provided to, for example without limitation, users who do not have insurance or elect not to bill insurance for such testing. In such cases, the billing parameters may be any testing elected by the user.

Regardless, if the test fits the billing parameters, then an option to order testing may be presented to the healthcare provider at the healthcare provider system 50. If not, then the test for the next genetic marker may be considered. Alternatively, or additionally, if the test fits the billing parameters, it may be automatically added to a list of ordered tests.

If the healthcare provider orders the test, or the test is automatically added, the appropriate wells 32 may be added to, or removed from, the testing device 30 to test for the specified genetic markers. Alternatively, or in addition, the appropriate wells 32 may be blocked or unblocked on the testing device 30 to test for the specified genetic markers. Once all identified tests are considered, instructions for assembly of the testing device 30 may be transmitted and the testing may be performed.

In exemplary embodiments, user information may be gathered, or presented, using one or more secured means. For example, without limitation, information may be gathered and entered into the personal electronic devices 51 running a secured browser application. The personal electronic devices 51 may comprise remote shunt down capabilities and a variety of security protocols, such as but not limited to, authentication, biometric scanning, single sign-on, or barcode scanning protocols may be utilized.

Other information gathered from the user may include scanned copies of insurance card and photo ID. Forms such as digital consent forms, questionnaires, and medical necessity forms may be digitally filled out, stored, and/or transmitted. The laboratory system 40 and/or the healthcare provider system 50 may be configured to generate a QR code, barcode, label, or other identifier for attachment to the genetic material gathering device 10, the genetic testing device, paperwork, some combination thereof, or the like. Scanning of the QR code, barcode, label, or another identifier may automatically retrieve the associated user information.

Figure 6:
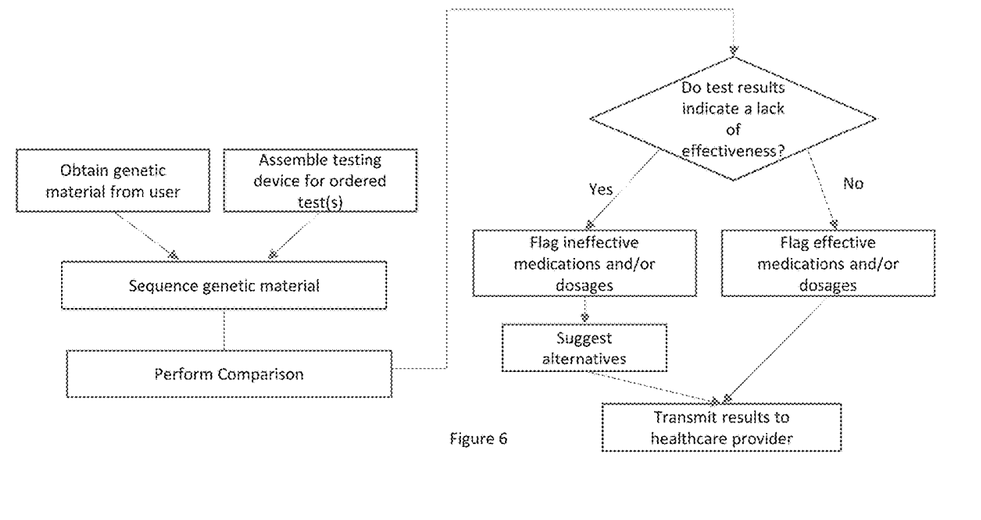
FIG. 6 is a simplified block diagram illustrating exemplary logic for performing testing and analyzing results.

FIG. 6 is a simplified block diagram illustrating exemplary logic for performing testing and analyzing results. Genetic material from the user may be gathered by way of the genetic material gathering device 10. A genetic testing device 30 comprising wells 32 for the ordered testing may be assembled. Such assembly may be performed manually or automatically. Such assembly may be performed concurrently, before, or after obtaining the genetic material. The genetic material may then be sequenced using the genetic sequencing device 20.

The testing may determine the presence or non-presence of the genetic markers for which the test is performed. The results of such testing may be transmitted to the laboratory system 40. The results may be compared against information stored in the laboratory system 40, or elsewhere, regarding the effectiveness of given medications in persons having or not having particular genetic markers. In particular, the results may be compared for each of the medications prescribed to the user, or likely to be prescribed to the user. Similarly, the results may be compared against information stored in the laboratory system 40, or elsewhere, regarding the need for particular dosages in persons having or not having particular genetic markers. In particular, the results may be compared for each of the medications and dosages prescribed to the user, or likely to be prescribed to the user. Such information may be gathered from one or more public or private sources such as, but not limited to, the human genome project.

The laboratory system 40 may flag ineffective medications or dosages. Likewise, the laboratory system 40 may flag effective medications or dosages. In exemplary embodiments, the results may be color coded. For example, without limitation, red color coding may indicate an ineffective medication or dosage. A yellow color coding may indicate the need to adjust the dosage or monitor use of the medication. A green color coding may indicate that the medication and dosage is acceptable. Other colors and types of coding are contemplated.

The results of the testing may be transmitted to the healthcare provider's system 50. The laboratory system 40 may be configured to automatically suggest alternative medications, or dosages, or treatment options for those medications flagged to be ineffective or requiring dosage adjustments. Furthermore, the healthcare provider's system 50 may be updated to reflect the ineffectiveness of the medications or dosages. For example, without limitation, ineffective medications may be flagged or otherwise coded as an allergy in the user's file. More specifically, ineffective medications may be identified in the message to the healthcare provider. For example, without limitation, this information may be added to the HL7 electronic results, such as but not limited to the PathX HL6 electronic communication, that are received with the test results and embedded into any .pdf type files generated from the HL7 file.

Alternatively, or in addition, additional parties may be notified of medications or dosages determined to be ineffective. Such parties may include, but are not limited to, pharmacists, project managers, healthcare practice administrators, insurance providers, users, other healthcare providers, other approved persons, and the like. The results of the testing may be transmitted to each parties' respective system.

One or more healthcare information exchanges may be utilized to provide information between various systems and individuals. For example, without limitation, the results of the testing may automatically be shared with the healthcare provider system 50 for each healthcare provider treating the user. Each healthcare provider treating the user may automatically be granted access to the results of the testing, such as by way of the respective healthcare provider's personal electronic device 51. In exemplary embodiments, the healthcare information exchange may provide two-way communication such that information may be transmitted to and from the laboratory system 40.

Figure 7:
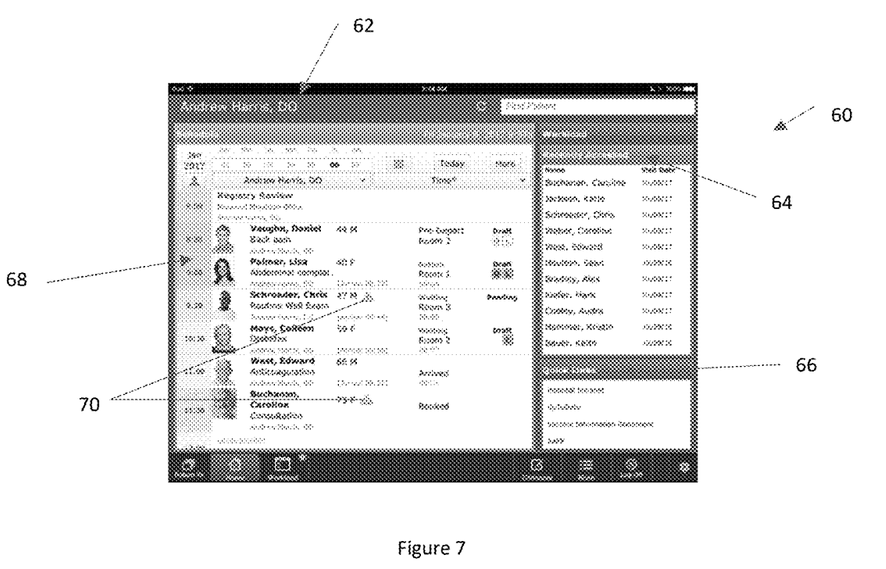
FIG. 7 is an exemplary healthcare provider interface.

FIG. 7 is an exemplary healthcare provider interface 60. The healthcare provider interface 60 may be shown on one or more personal electronic devices 51 in electronic communication with the healthcare provider system 50. The personal electronic devices 51 may be computers, smartphones, tablets, or the like. The interface 60 may provide results for one or more patients. The interface 60 may alternatively, or in addition, provide the results for multiple medications for a one or more patients. In exemplary embodiments, the results may be presented with the clinical consequences of prescribing each of the medications. For example, without limitation, the interface 60 may inform the healthcare provider of whether the prescribed medication is likely to be effective, partially effective, wholly ineffective, or the like. The healthcare provider interface 60 may be updated for each individual healthcare provider user 62. The healthcare provider's recently accessed files may be identified 64. A quick links section 66 may include a link to the portal for test ordering and results. A schedule 68 may include one or more indicators 70 which patient(s) have possible warnings associated with their test results. For example, without limitation, the results may be color coded.

In other exemplary embodiments, indicators 70 may be presented in the form of alerts. Such alerts may be pop-ups, warning signals, electronic messages, or the like. Such indicators 70 may be generated upon the receipt of results which indicate that the healthcare provider has prescribed a drug to a patient known to be a non-responder to such medications, the presence of abnormal result or range, the prescription of a drug known to cause an allergic effect in the patient, or the prescription of a drug which may potentially cause an interaction with a drug previously prescribed to the patient, or with a disease the patient is diagnosed with as understood in view of the analyzed genetic information. Other clinical information may be transmitted and displayed on the interface 60 such as, without limitation, an explanation of the results.

Figure 8:
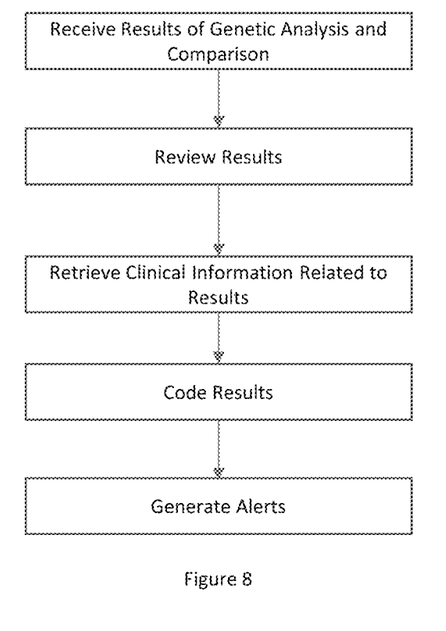
FIG. 8 is a simplified block diagram illustrating exemplary logic for analyzing results and generating alerts.

FIG. 8 is a simplified block diagram illustrating exemplary logic for analyzing results and generating alerts. Once the results of the genetic analysis are received, they may be reviewed. The review may include a comparison against information known about the patient, for example, by analyzing the patient's medical records. For example, without limitation, the results may be reviewed to determine if the healthcare provider has prescribed a drug to a patient known to be a non-responder to such medications, if the results include an abnormal result or range, if the healthcare provider has prescribed a drug known to cause an allergic effect in the patient, or if the healthcare provider has prescribed a drug which may potentially cause an interaction in view of the analyzed genetic information. The clinical information required to support this analysis may be retrieved from one or more databases, such as but not limited to, the healthcare provider system 50 or a database comprising various known medical information such as known drug interactions based on genetic makeup, normal results or ranges for various medical tests, and the like. The results of this review may be used to code the results displayed at the interface 60 or generate alerts as appropriate.

The comparison, analysis, and the like described herein may be performed at the laboratory system 40 or at the healthcare provider system 50. It is contemplated that any type of clinical information may be transmitted for display at the interface 60.

The clinical consequence of prescription, in exemplary embodiments, may be added to the electronic results and embedded into a single file for transmission to the healthcare provider system 50. This may remove the need for use of multiple file types between the laboratory system 40, the healthcare provider system 50, and the electronic displays or individual systems 51. This may alternatively, or in addition, remove the need for multiple file types to be transmitted to one of the aforementioned systems. For example, one file with the results and another file with any alerts or other clinical information, though such an embodiment is contemplated. In exemplary embodiments, the results and all other related clinical information may be transmitted in a single standardized file, such an HL7 type file, though any file type is contemplated. This may permit the report to be integrated into any EMR system.

The coding and alerts described herein may be individualized based on the preferences of each user or entity. For example, when communicating results to a first healthcare provider system 50, alerts may be generated only when certain predetermined conditions are met. Likewise, when communicating results to a second healthcare provider system 50 alerts may be generated only when other predetermined conditions are met which may be the same or different from (with some overlap, complete overlap, or no overlap) with the predetermined conditions used to generate alerts for communications to the first healthcare provider system 50. Similarly, preferences may be altered for each personal electronic device 51.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

Certain operations described herein may be performed by one or more electronic devices. Each electronic device may comprise one or more processors, electronic storage devices, executable software instructions, and the like configured to perform the operations described herein. The electronic devices may be general purpose computers of specialized computing device. The electronic devices may be personal computers, smartphone, tablets, databases, servers, or the like. The electronic connections described herein may be accomplished by wired or wireless means.

What is claimed is:

1. A system for alerting a healthcare provider to ineffective medications in real time, said system comprising:
    a healthcare provider system comprising an electronic display and an electronic storage device comprising data regarding medications prescribed by, or likely to be prescribed by, the healthcare provider to each of a number of patients treated by the healthcare provider;
    a database comprising data regarding medications known to be ineffective in persons having particular genetic markers; and
    a laboratory system in electronic communication with the healthcare provider system and the database, wherein the laboratory system comprises a processor and an electronic storage device comprising software instructions, which when executed, configure the processor to:
        receive genetic testing results comprising genetic markers of a patient from said number of patients treated by the healthcare provider;
        query the database to determine whether any medications in the list of medication prescribed by, or likely to be prescribed by, the healthcare provider to the patient are known to be ineffective in persons having the same genetic markers as the patient;
        generate and transmit a report to the healthcare provider system indicating which of the medications in the list of medication prescribed by, or likely to be prescribed by, the healthcare provider to the patient are known to be ineffective in persons having the same genetic markers as the patient; and
        receive, from the legacy healthcare provider system, a list of ordered tests;
    wherein said healthcare provider system comprises a processor and executable software instructions stored at the electronic storage device which, when executed, configure the processor to:
        flag each of the medications indicated in the report at the healthcare provider system; and
        automatically display an alert at said electronic display upon electronic indication of prescription of any of the flagged medications;
    an automated genetic testing device assembly machine, wherein said laboratory system comprises additional software instructions stored at the electronic storage device, which when executed, configure the processor to generate and electronically transmit instructions to the automated genetic testing device assembly machine which cause the automated genetic testing device assembly machine to commence at least partially automated assembly of a genetic testing device in accordance with the list of ordered tests.

2. The system of claim 1 wherein:
said healthcare provider system comprises an electronic medical record system; and
each of said medications is flagged as an allergy at the electronic medical record system.

3. The system of claim 2 wherein:
said healthcare provider system comprises additional software instructions stored at the electronic storage device, which when executed, configure the processor to:
    display a list comprising identifying information for each of said number of patients treated by the healthcare provider; and
    display an indicator in association with the patient which indicates whether one or more medications prescribed, or likely to be prescribed, to said patient are known to be ineffective in persons having the same genetic markers as the patient.

4. The system of claim 1 wherein:
said healthcare provider system further comprises diagnostic codes and insurance information for each of said number of patients treated by the healthcare provider stored at the electronic storage device; and
said laboratory system comprises additional software instructions stored at the electronic storage device, which when executed, configure the processor to:
receive said diagnostic codes and said insurance information for the patient;
determine which genetic tests are covered by the patient's insurance; and
display a prompt at said healthcare provider system to add genetic tests covered by the patient's insurance to the list of ordered tests.

5. The system of claim 1 wherein:
said database further comprises a list of alternative medications; and
said laboratory system comprises additional software instructions stored at the electronic storage device, which when executed, configure the processor to display a suggested alternative medication, based on said list of alternative medications, for each medication prescribed by, or likely to be prescribed by, the healthcare provider to the patient which are known to be ineffective in persons having the same genetic markers as the patient.

6. The system of claim 1 wherein:
said healthcare provider system further comprises diagnostic codes for each of said number of patients treated by the healthcare provider stored at the electronic storage device;
said database further comprises a list of alternative treatment options; and
said laboratory system comprises additional software instructions stored at the electronic storage device, which when executed, configure the processor to display a suggested alternative treatment option, based on said list of alternative treatment options, for each condition diagnosed by the healthcare provider which is known to normally require medications which are known to be ineffective in persons having the same genetic markers as the patient.

7. The system of claim 1 further comprising:
a genetic material gathering device;
a genetic sequencing device, wherein said genetic sequencing device is configured to receive the genetic material gathering device, wherein said genetic sequencing device is in electronic communication with said laboratory system; and
additional software instructions stored at the electronic storage device of the laboratory system, which when executed, configure the processor to:
receive an order for genetic testing; and
electronically generate and transmit instructions to said genetic sequencing device to perform said ordered testing in an at least partially automated fashion.

8. The system of claim 1 wherein:
said laboratory system comprises additional software instructions stored at the electronic storage device, which when executed, configure the processor to generate a web-based portal at the electronic display of the healthcare provider system.

9. The system of claim 1 wherein:
said database further comprises diagnostic codes and a list of commonly prescribed medications associated with said diagnostic codes; and
said laboratory system comprises additional software instructions stored at the electronic storage device, which when executed, configure the processor to:
receive diagnostic codes from the healthcare provider system; and
query the database to retrieve the commonly prescribed medications associated with the received diagnostic codes to determine the medications likely to be prescribed to the patient.

10. The system of claim 1 wherein:
said healthcare provider system comprises a list of medication prescribed to the patient and insurance information for each of said number of patients treated by the healthcare provider stored at the electronic storage device;
said database further comprises a list of tests for genetic markers known to affect the efficacy of various medications; and
said laboratory system comprises additional software instructions stored at the electronic storage device, which when executed, configure the processor to:
receive the prescribed medications from the healthcare provider system;
query the database to retrieve the tests for genetic markers known to affect the efficacy of the prescribed medications;
receive insurance information for the patient;
further identify certain of the identified tests which are covered by the patient's insurance; and
transmit a list of the further identified tests to the healthcare provider system.

11. A system for alerting a number of healthcare providers to ineffective medications and available, covered genetic efficacy testing in real time, said system comprising:
a number of electronic medical records systems ("EMRs"), each associated with one or more of a number healthcare practices and each comprising an electronic display and data regarding medications prescribed by one or more healthcare providers of one of the healthcare practices to each of a number of patients treated by the healthcare providers of the healthcare practice, diagnostic codes for each of the patients, and insurance information for each of the patients;
a number of personal electronic devices in electronic communication with each of said EMRs;
a database comprising data regarding medications known to be ineffective in persons having particular genetic markers and a list of alternative medications and treatment options;
a healthcare information exchange system in electronic communication with each of the EMRs of each of the healthcare practices;
a genetic sequencing machine;
an automated genetic testing device assembly machine; and
a laboratory system in electronic communication with the healthcare information exchange system, the database, the genetic sequencing machine, and the genetic testing device assembly machine, wherein the laboratory system comprises a processor and an electronic storage device comprising software instructions, which when executed, configure the processor to:
receive the insurance information and the diagnostic codes for the particular patient;

determine available and covered genetic testing for the particular patient;

automatically order the available and covered genetic testing;

generate and transmit electronic instructions to the automated genetic testing device assembly machine which, when received and executed by the automated genetic testing device assembly machine, cause the at least partially automated assembly of a genetic testing device in accordance with the ordered testing at the automated genetic testing device assembly machine;

transmit electronic instructions to the genetic sequencing machine for at least partially automated performance of the ordered testing on the genetic testing device;

receive genetic testing results from the genetic sequencing machine comprising genetic markers of the particular patient;

query the database to determine whether any medications in the list of medication prescribed to the particular patient are known to be ineffective in persons having the same genetic markers as the particular patient (the "ineffective medications");

query the database to determine alternative medications and treatment options for each of the ineffective medications;

generate a report comprising the ineffective medications, the alternative medications, and the alternative treatment options for each of the ineffective medications; and transmit the report to said healthcare information exchange;

wherein said healthcare information exchange is configured to transmit the report to each of the EMRs associated with a healthcare practice associated with one or more healthcare providers treating said particular patient;

wherein each of said personal electronic devices in communication with the respective EMR receiving said report are configured to:
  display said report in a web-based portal on the respective electronic display; and
  automatically flag all of said ineffective medications in said report as an allergy at the respective EMR;

wherein each of said EMRs are configured to:
  receive data indicating prescription of additional medications for the particular patient; and
  automatically generate an alert when one or more of said additional medications are flagged.

12. The system of claim 11 wherein:

each of said personal electronic devices are configured to display, in the web-based portal, a list comprising identifying information for each of said number of patients scheduled to be seen by the respective healthcare provider on a given day; and each of said EMRs comprise software instructions stored at an electronic storage device, which when executed, configure a processor to display all of the alerts for the patients in the form of an indicator, in the web-based portal, including in association with the particular patient for whom one of the alerts was received which indicates that one or more medications are prescribed to said particular patient which are known to be ineffective in persons having the same genetic markers as the particular patient.

* * * * *